United States Patent [19]
Meller et al.

[11] Patent Number: 5,160,263
[45] Date of Patent: * Nov. 3, 1992

[54] DISPOSABLE RIGHT ANGLE DENTAL HANDPIECE

[75] Inventors: Moshe Meller, 175 Oberlin Ave., Lakewood, N.J. 08701; Michael Feldman, Howell, N.J.

[73] Assignee: Moshe Meller, Lakewood, N.J.

[*] Notice: The portion of the term of this patent subsequent to Apr. 16, 2008 has been disclaimed.

[21] Appl. No.: 683,251

[22] Filed: Apr. 10, 1991

Related U.S. Application Data

[63] Continuation of Ser. No. 502,454, Mar. 30, 1990, Pat. No. 5,007,832.

[51] Int. Cl.⁵ .............................................. A61C 1/08
[52] U.S. Cl. ........................................ 433/125; 433/126
[58] Field of Search .............. 433/114, 116, 125, 126, 433/127, 128, 129, 133

[56] References Cited

U.S. PATENT DOCUMENTS

| | | | |
|---|---|---|---|
| 1,982,336 | 11/1934 | Wiseman | 433/125 |
| 3,727,313 | 4/1973 | Graham | 433/125 |
| 3,798,777 | 3/1974 | Reiter | 433/125 |
| 4,245,985 | 1/1981 | Eibofner | 433/126 |
| 4,365,956 | 12/1982 | Bailey | 433/125 |
| 4,449,932 | 5/1984 | Lustig | 433/126 |
| 4,544,356 | 10/1985 | Gardella et al. | 433/125 |
| 4,604,058 | 8/1986 | Fisher et al. | 433/125 |

FOREIGN PATENT DOCUMENTS

| | | | |
|---|---|---|---|
| 508696 | 4/1928 | Fed. Rep. of Germany | 433/126 |
| 3227417 | 2/1983 | Fed. Rep. of Germany | 433/126 |
| 2584918 | 1/1987 | France | 433/126 |

Primary Examiner—John J. Wilson
Attorney, Agent, or Firm—Frishauf, Holtz, Goodman & Woodward

[57] ABSTRACT

A disposable right angle dental handpiece comprises a disposable plastic outer housing having an elongated opening therein for receiving a drive shaft mechanism which is preferably made of metal. The drive shaft mechanism is connected to the disposable outer plastic housing by means of a quick connect-quick disconnect mechanism. The outer housing also contains a gear which is engaged with a gear at the end of the drive shaft mechanism, a working member being connected to the gear for being driven by the drive shaft member. The drive shaft member is connectable to the dental tool for being driven thereby.

14 Claims, 2 Drawing Sheets

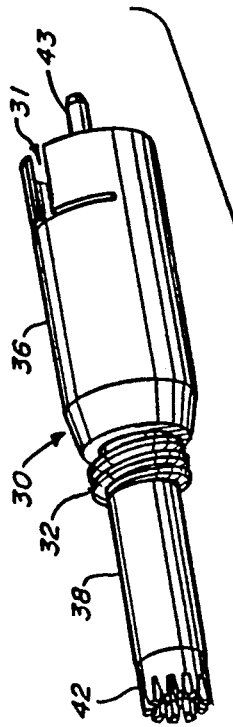
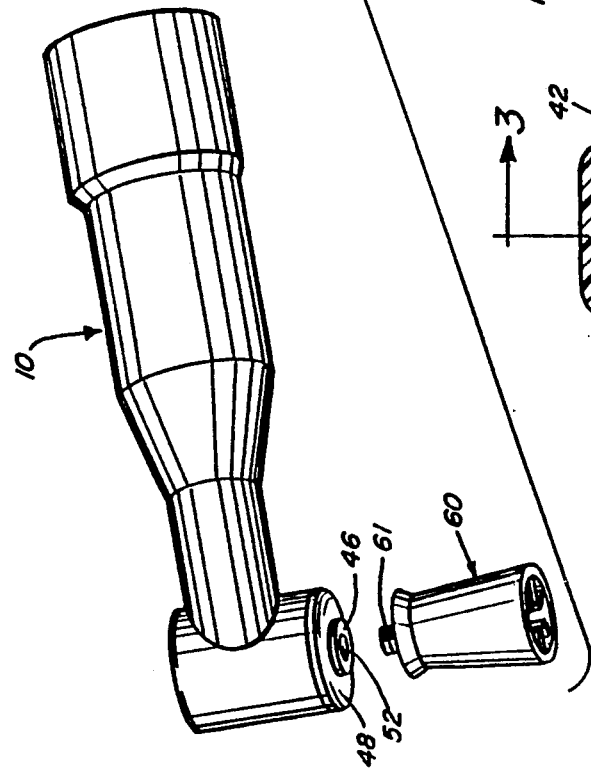
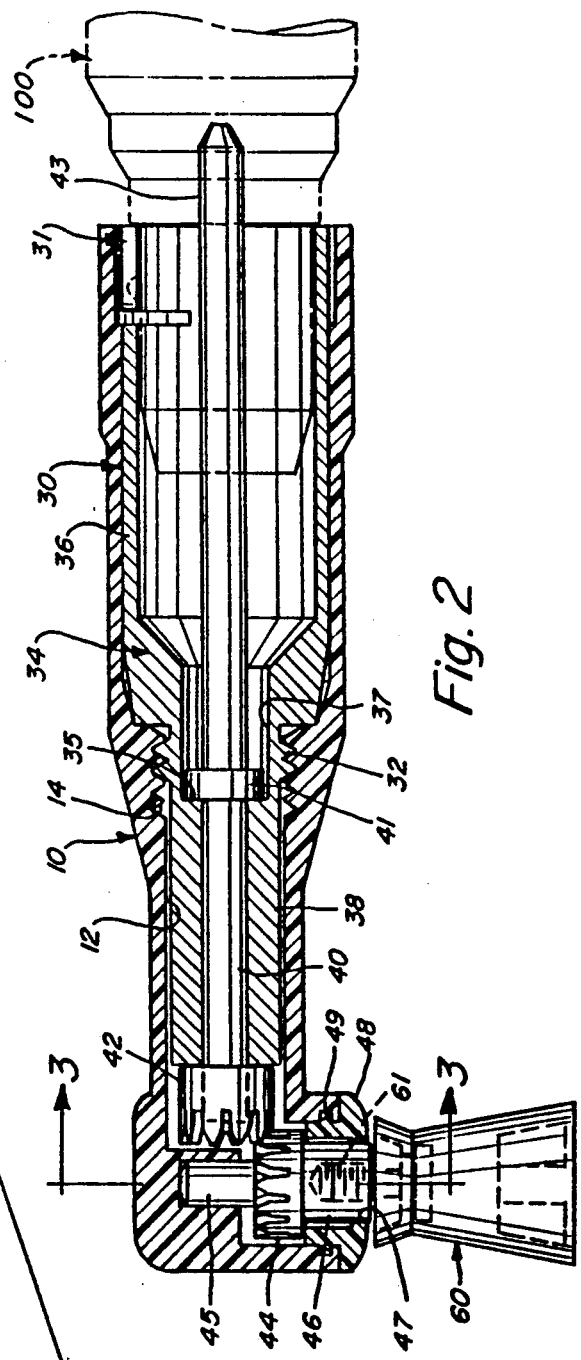
Fig. 1
Fig. 2

DISPOSABLE RIGHT ANGLE DENTAL HANDPIECE

This is a continuation of application Ser. No. 07/502,454 filed Mar. 30, 1990, now U.S. Pat. No. 5,007,832.

BACKGROUND OF THE INVENTION

This invention relates to a disposable dental handpiece, and more particularly to a disposable right angle dental prophylaxis handpiece.

Disposable dental prophylaxis right angle hand pieces are known, for example, from U.S. Pat. No. 3,727,313, the entire contents of which are incorporated herein by reference. Such disposable dental handpieces are desirable since the portions that come into contact with a patient may be thrown away after use, thereby eliminating the expense of sterilizing the handpiece and also eliminating the risk of incomplete sterilization and/or transfer of infection. At present, the transfer of infection is of utmost concern.

The disposable right angle hand piece of U.S. Pat. No. 3,727,313 is disadvantageous in that all of the internal parts thereof are made of disposable plastic materials, and thus the device provides poor operability. The shaft itself is made of plastic and provides poor engagement with the drive mechanism. Moreover, plastic particles wear off the shaft and cause damage to the internal parts of the handpiece and may also possibly damage the drive mechanism of the dental equipment. The plastic gears are inferior and provide poor power transmission between the drive shaft and the elastic rubber working cup 24. Also, the plastic gears tend to wear during use, even for a short time.

The object of the present invention is to provide an improved disposable right angle prophylaxis handpieces which has improved operability, which overcomes the disadvantages inherent in the design of known devices such as that disclosed in U.S. Pat. No. 3,727,313.

SUMMARY OF THE INVENTION

According to the present invention, a disposable right angle handpiece comprises an outer housing made of disposable plastic material and having an elongated opening therein for receiving a drive shaft means; a cavity in said housing for receiving a driven gear member; means coupling a working member to said driven gear member for performing a working operation in an oral cavity of a patient; a drive shaft means, preferably made of metal, in said elongated opening of said outer housing and having means at one end thereof for engaging with a dental drive means of a dental tool, and being rotatable within said housing, and having a gear at the distal end thereof which engages with said driven gear; and means for coupling said drive shaft means to said housing for securing said drive shaft means in said housing in engagement with said driven gear during use, and for permitting disengagement of said drive shaft means from said housing for disposal of said housing.

BRIEF DESCRIPTION OF THE DRAWINGS

FIG. 1 is a disassembled perspective view of a disposable right angle dental handpiece according to the present invention;

FIG. 2 is a longitudinal cross-sectional view thereof in the assembled state;

DETAILED DESCRIPTION

Referring to FIGS. 1 and 2, the right angle dental handpiece of the present invention comprises a hollow outer housing 10 which has an elongated opening therein for receiving a drive member 30 therein. A working member, for example, a conventional elastic rubber cup 60, is connected to the distal end of the housing 10 so as to be rotated via a gear arrangement by means of the drive member 30. The outer housing 10 is preferably made of plastic material and is disposable. The drive member 30 is preferably made of metallic material, such as brass, so that it can be re-used or disposed of after each use. The design of the drive member 30 is relatively simple and inexpensive to manufacture. Therefore, even if it is disposed of often, the design is still economical.

Figure 3:
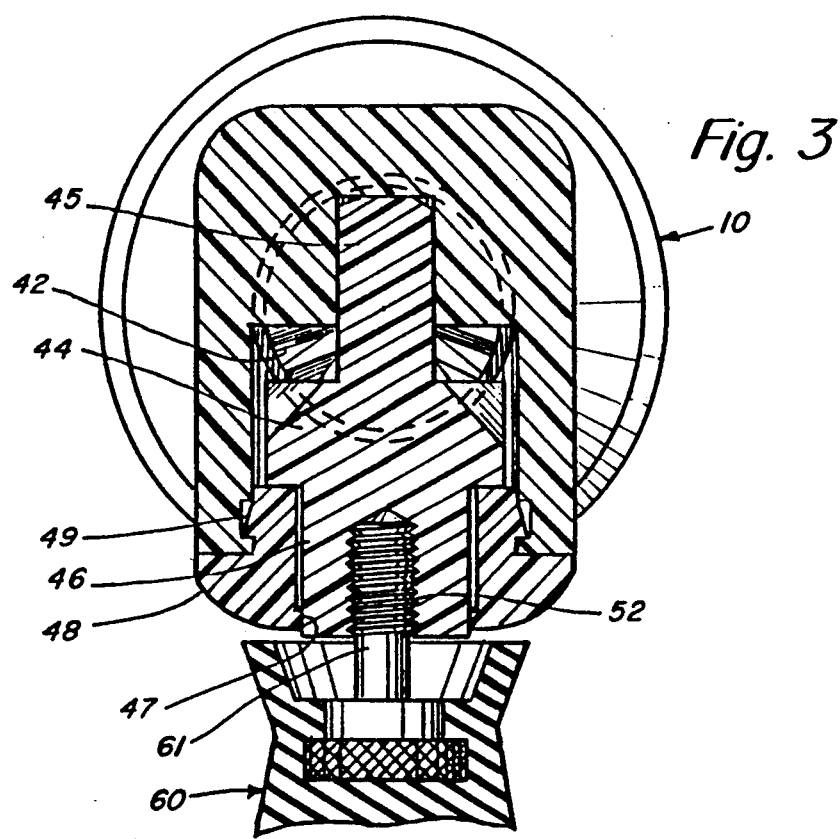
FIG. 3 is a cross-sectional view thereof taken along line 3—3 in FIG. 2.

Referring to FIGS. 2 and 3, the outer plastic housing 10 has an inner elongated opening 12 formed therein for receiving the drive member 30. The drive member 30 has a threaded portion 32 which threadably engages a threaded portion 14 of housing 10. The drive member 30 comprises an outer housing portion 34 which comprises a larger diameter portion 36 and a smaller diameter portion 38 which are integrally formed with the threaded portion 32 interposed therebetween. A shaft 40 extends through said drive member housing 34 and has a bearing 41 at an intermediate portion thereof for rotatably engaging an inner surface 37 of the housing 37 and for engaging an end-stop surface 35 of the housing 34 to limit the forward axial movement of the shaft 40. The bearing 41 serves as a sleeve-type bearing with the inner surface portion 37 of the housing 34. The contact portions between said shaft 40 and housing portion 38 may also be considered as sleeve-type bearings which rotatably support shaft 40.

A gear 42 is fixed (i.e., press fit) to the distal end of shaft 40 for driving the cup 60, as will be explained hereinbelow. The gear 42 engages a forward wall of the small diameter portion 38 to act as a stop mechanism to prevent rearward movement of the shaft 40 relative to the housing 34. The gear 42 preferably has a hole therein which is press fit over the forward extending end of shaft 40. The opposite or proximal end of the shaft 40 extends outwardly rearwardly of the housing 30 and engages the dental drill or dental tool handpiece 100 so as to be rotated by a motor or other drive means connected thereto, in a conventional manner. The end 43 of the shaft 40 is connected to the drill tool 100 in a conventional manner, for example by means of a chuck or the like, in the same manner as in U.S. Pat. No. 3,727,313. Housing 30 has a T-shaped slit or opening 31 formed therein for engagement with a conventional locking device of a dental hand tool 100 to secure the handpiece of the present invention onto the dental tool 100. A detailed explanation of this locking device is unnecessary, since it is conventional. Other types of connecting mechanisms or units other than as shown in FIG. 2 can be used. Shaft end 43 would be modified accordingly, as would opening 31, to fit the desired connecting apparatus at the drive end of the dental tool handpiece.

The distal or head end of the housing 10 defines a cavity containing a rotatable gear 44 which meshes with gear 42 so as to be rotated thereby. The gear 44 is preferably made of metal, but could be made of plastic material, and has a shaft 45 extending upwardly therefrom for rotation within a bearing opening in the distal or head end of the housing 10. The opposite end 46 of the gear 44 rotates against a bearing surface 47 of the cap 48 of the housing 10. The cap 48 is preferably press fit into an opening in the distal end of the housing 10 and has a circumferential protrusion 49 thereon for snap-type engagement into a corresponding circumferential groove in the head end of the housing 10. Alternatively, the projection 49 can be provided on the inner surface of the opening adjacent the cap 48, and the cap 48 can be provided with a circumferential groove thereon for receiving the projection to lock the cap 48 on the housing. This arrangement provides an effective seal for preventing contamination from entering into the interior of the housing 10 and prevents wearing of the gears, shafts and bearings within the housing 10.

The flexible cup 60 preferably has a threaded shaft 61 (preferably metal, but it could be plastic) extending therefrom which is threadably inserted into a threaded opening 52 in gear member 46 so that upon rotation of the gear 46, the cup is similarly rotated. The direction of threads is such as to tighten the threaded engagement during rotation of the cup by the shaft 40.

Figure 4:
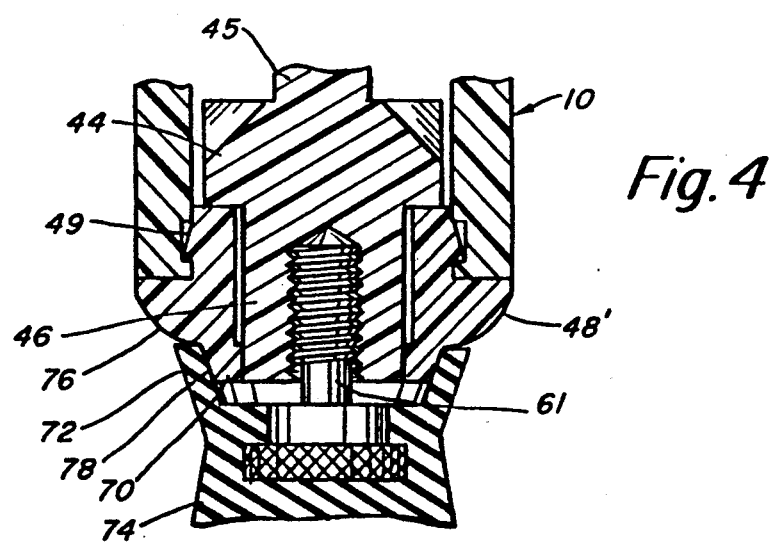
FIG. 4 is a cross-sectional view similar to FIG. 3, but illustrating a modified arrangement of the present invention.

The contact area at the surface portion 47 and the gear 46 is sufficiently close (i.e., the clearance therebetween is sufficiently small) that contamination is effectively prevented from entering within the interior of the housing 10. However, in order to improve the seal between the distal end of the housing and the working member 60, the housing can be modified as shown in FIG. 4 by forming a downward projection 70 at the distal end of the housing (on cap 48) and by forming an upward projection 72 on the flexible cup 74. The upper tip end of the upward projection 72 of the cup 74 is dimensioned so as to be very close to the upper wall 76 of the distal end of the housing 10. Also, an elongated surface sliding contact area is provided between the upper projection 72 of the cup 74 and the outer surface portion of housing projection 70, as shown at 78 in FIG. 4. The upwardly extending portion 72 of the cup 74 is resilient, thereby improving the seal between the downward projection 70 of the housing and the upwardly projecting portion 72, thereby further preventing entry of contamination into the interior of the housing.

In use, the assembled dental tool of the present invention (for example, as assembled in FIG. 2) is mounted on the end of a conventional dental tool handpiece 100 (see FIG. 2) and is locked thereon by means of the engagement opening 31. The end 43 of the shaft 40 is engaged in the chuck of the dental tool 100 in a conventional manner. As mentioned above, other types of interconnecting techniques between the shaft 40 and the dental tool 100 can be provided, depending upon the construction of the particular dental tool handpiece 100 with which the device of the present invention is used. As required, the device of the present invention is fabricated with different types of dental tool connecting means, and is not limited to the partieular construction shown in the present drawings.

After the device of the present invention is mounted on the dental tool handpiece 100, it is used in the normal manner by the practitioner. After use, the outer housing and the working cup 60 can be easily removed, for example, by twisting off the outer housing 10 from the drive shaft mechanism 30. The threads 32, 37 are of a quick connect-quick disconnect type, meaning that they are preferably designed so that only a half turn or three quarters of a turn thereof will disengage the outer housing 10 from the drive shaft portion 30. The device is preferably disassembled while it is still connected to the dental tool 100 so that the dental tool 100 anchors the drive shaft member 30 in place, and the housing 10 is more easily removed therefrom. Still further, the head end of the right angle dental handpiece of the present invention, and the projecting cup 60, provides convenient gripping and leverage producing areas to facilitate turning of the outer housing 10 for removal thereof. The outer housing 10, with its internal gear 46, along with the working cup 60 can then be readily disposed of, leaving only the metallic drive shaft portion 30 connected to the drill 100. Since contamination is effectively prevented from entering into the interior of the housing 10, the drive shaft portion 30, being made of metal, can be reused. If desired, or if contamination has inadvertently entered the interior of the housing 10, the drive shaft mechanism 30 can be sterilized for reuse in an easy manner.

Since the internal drive shaft portion 30 is made of metal, and has extremely good durability and operability, the device of the present invention provides the advantages of lost cost disposability while also providing excellent operability of the device without the problems inherent in the all plastic disposable devices of the type disclosed ion U.S. Pat. No. 3,727,313.

While the threads 32, 37 are shown as providing the interconnection between the drive mechanism 30 and the outer housing 10, various other quick connect-quick disconnect mechanisms could be used, such as a bayonet connection, snap-type connection, ball and socket-type connection, or the like, could be used. The threaded portions are shown by way of example and is not limiting of the present inventive concept.

The outer disposable housing 10 of the present invention is made of an FDA approved plastic material, such a nylon No. 6/6. However, other FDA approved plastic materials which are low in cost and sufficiently rugged can be used. The drive shaft means including the housing 34 and drive shaft 40 are preferably made of metal material such as brass, brass coated with chrome, brass coated with nickel, or other suitable metallic materials. The gears 42, 44 are preferably made of stainless steel or other hard metal material, but could also be made of brass, brass coated with chrome or nickel, or the like. The shaft 45 of gear 44 may also be made of the same material as gear 44. The housing 34, shaft 40 and gears 42, 44 may be made from a very hard, rugged, durable synthetic material which has good wear characteristics, such as acetal, Delrin (a nylon material), polycarbonate (such as Noryl or Lexan) or other sufficiently hard or reinforced plastic (i.e., reinforced with glass fibers, graphite fibers, or other suitable material) suitable for use in the mouth and approved by the FDA. Metal, however, is preferred for housing 34, shaft 40 and gears 42, 44 to produce the best performance, durability, operability, and autoclaveability when the drive means 34, 40, 42 is to be re-used a plurality of times.

While the invention has been described above with respect to specific embodiments, various modifications and alterations can be made within the scope of the invention as defined by the appended claims.

We claim:

1. A disposable dental handpiece comprising:

an outer housing made of a disposable molded plastic material and having an elongated opening therein for receiving a drive shaft means, said outer housing being disposable after use thereof;

a cavity in said outer housing for receiving a driven rotatable gear member;

means for coupling a working member to said driven gear member for performing a working operation in an oral cavity of a patient;

a re-usable drive shaft means removably mounted in said elongated opening in said outer housing, said re-usable drive shaft means including:

a rotatable drive shaft in said outer housing and being rotatable relative to said outer housing, said drive shaft being driven at one end portion thereof by a dental drive means of a dental tool, so as to be rotatably driven within said outer housing; and a driving gear at a distal end portion of said drive shaft, which distal end portion is opposite from said one end portion thereof, for engaging with said driven gear;

means for removably coupling said re-usable drive shaft means to said outer housing for removably securing said re-usable drive shaft means in said elongated opening of said outer housing such that said driving gear is in engagement with said driven gear during use, and for permitting disengagement of said re-usable drive shaft means from said outer housing for disposal of said outer housing, said removably coupling means not penetrating through said outer housing, and including an external screw thread portion on said re-usable drive shaft means which is threadably engageable with a mating internal screw thread portion inside of said cavity in said outer housing to permit threaded engagement and disengagement of said re-usable drive shaft means from said outer housing and for maintaining said drive shaft and outer housing in fixed longitudinal position relative to said dental drive means and for maintaining said driven and driving gears in meshing engagement while preventing relative rotation between said outer housing and said screw thread portion of said re-usable drive shaft means; and said outer housing comprising means for non-rotationally coupling said outer housing to said dental drive means of said dental tool, so as to rotationally drive said rotatable drive shaft in said outer housing by means of said dental drive means of said dental tool.

2. The dental handpiece of claim 1, wherein said outer housing is a one piece molded structure which is molded as a single piece.

3. The dental handpiece of claim 2, wherein said re-usable drive shaft means is disengageable and removable from said outer housing without disassembly of said one piece molded structure.

4. The dental handpiece of claim 1, wherein said working member comprises a flexible cup for dental prophylaxis use.

5. The dental handpiece of claim 1, wherein said drive shaft means is made of metal material.

6. The dental handpiece of claim 1, further comprising a drive shaft housing interposed between said outer housing and said drive shaft, said drive shaft being mounted within said drive shaft housing and being rotatable relative to said drive shaft housing, said external screw thread portion being provided on said drive shaft housing.

7. The dental handpiece of claim 6, wherein said drive shaft housing is made of metal material.

8. The dental handpiece of claim 7, wherein said re-usable drive shaft means further comprises bearing means for rotatably supporting said drive shaft within said drive shaft housing.

9. The dental handpiece of claim 6, wherein said driving gear is made of metal material.

10. The dental handpiece of claim 9, wherein said driven gear is made of metal material.

11. The dental handpiece of claim 6, wherein said drive shaft housing is metallic, and said re-usable drive shaft means further comprises bearing means for rotatably supporting said drive shaft within said metallic drive shaft housing.

12. The dental handpiece of claim 11, wherein said drive shaft is made of metal material.

13. The dental handpiece of claim 1, wherein said outer housing has a projecting portion thereon in the vicinity of said coupling means for a working member, and wherein said working member has a projecting skirt member adjacent to and surrounding said projecting portion for improving a seal between said outer housing and said working member.

14. The dental handpiece of claim 1, wherein said re-usable drive shaft means is disengageable and removable from said outer housing without disassembly of said outer housing.

* * * * *